US010829508B2

(12) United States Patent
Papadakis et al.

(10) Patent No.: US 10,829,508 B2
(45) Date of Patent: Nov. 10, 2020

(54) FERMENTATIVE PRODUCTION OF OLIGOSACCHARIDES

(71) Applicant: GLYCOM A/S, Hørsholm (DK)

(72) Inventors: Manos Papadakis, København (DK); Margit Pedersen, Roskilde (DK); Katrine Bych, Valby (DK)

(73) Assignee: GLYCOM A/S, Hørsholm (DK)

( * ) Notice: Subject to any disclaimer, the term of this patent is extended or adjusted under 35 U.S.C. 154(b) by 38 days.

(21) Appl. No.: 16/063,465

(22) PCT Filed: Dec. 19, 2016

(86) PCT No.: PCT/DK2016/050447
§ 371 (c)(1),
(2) Date: Jun. 18, 2018

(87) PCT Pub. No.: WO2017/101958
PCT Pub. Date: Jun. 22, 2017

(65) Prior Publication Data
US 2018/0371001 A1 Dec. 27, 2018

(30) Foreign Application Priority Data
Dec. 18, 2015 (DK) .................. 2015 70834

(51) Int. Cl.
*C07H 3/06* (2006.01)
*C12P 19/18* (2006.01)
*C12N 9/10* (2006.01)
*C07H 1/00* (2006.01)
*C07H 3/02* (2006.01)
*C12N 15/70* (2006.01)

(52) U.S. Cl.
CPC .............. *C07H 3/06* (2013.01); *C07H 1/00* (2013.01); *C07H 3/02* (2013.01); *C12N 9/1048* (2013.01); *C12N 9/1051* (2013.01); *C12N 9/1081* (2013.01); *C12N 15/70* (2013.01); *C12P 19/18* (2013.01); *C12Y 204/99001* (2013.01)

(58) Field of Classification Search
None
See application file for complete search history.

(56) References Cited

U.S. PATENT DOCUMENTS

| 5,198,343 A | 3/1993 | Degryse |
| 7,521,212 B1 | 4/2009 | Samain et al. |
| 2004/0234984 A1 | 11/2004 | Isaksson et al. |
| 2014/0031541 A1 | 1/2014 | Heidtman et al. |

FOREIGN PATENT DOCUMENTS

| EP | 0258118 A1 | 3/1988 |
| EP | 1911850 A1 | 4/2008 |
| WO | 0104341 A1 | 1/2001 |
| WO | 02059292 A2 | 8/2002 |
| WO | 2007101862 A2 | 9/2007 |
| WO | 2010070104 A1 | 6/2010 |
| WO | 2012112777 A2 | 8/2012 |
| WO | 2013182206 A1 | 12/2013 |
| WO | 2014048439 A1 | 4/2014 |
| WO | 2015032412 A1 | 3/2015 |
| WO | 2015032413 A1 | 3/2015 |
| WO | 2015036138 A1 | 3/2015 |
| WO | 2015049331 A1 | 4/2015 |
| WO | 2015106943 A1 | 7/2015 |
| WO | 2015150328 A1 | 10/2015 |
| WO | 2015175801 A1 | 11/2015 |
| WO | 2015197082 A1 | 12/2015 |

OTHER PUBLICATIONS

Shelver, D., et al., "Carbon Monoxide-Induced Activation of Gene Expression in Rhodospirillum rubrum Requires the Product of cooA, a Member of the Cyclic AMP Receptor Protein Family of Transcriptional Regulators," Journal of Bacteriology, 1995, vol. 177(8), pp. 2157-2163.

Baumgärtner, F., et al., "Construction of *Escherichia coli* strains with chromosomally integrated expression cassettes for the synthesis of 2'-fucosyllactose," Microbial Cell Factories, 2013, vol. 12:40, 13 pages.

Baumgärtner, F., et al., "Synthesis of the Human Milk Oligosaccharide Lacto-N-Tetraose in Metabolically Engineered, Plasmid-Free *E. coil*," ChemBioChem, 2014, vol. 15, pp. 1896-1900.

Dong, W.R. et al., "Novel Antibiotic-Free Plasmid Selection System Based on Complementation of Host Auxotrophy in the NAD De Novo Synthesis Pathway," Applied and Environmental Microbiology, 2010, vol. 76(7), pp. 2295-2303.

Drouillard, S., et al., "Large-Scale Synthesis of H-Antigen Oligosaccharides by Expressing Helicobacter pylori α1,2-Fucosyltransferase in Metabolically Engineered *Escherichia coli* Cells," Angew. Chem. Int. Ed., 2006, vol. 45, pp. 1778-1780.

Fort, S., et al., "Biosynthesis of conjugatable saccharidic moieties of GM2 and GM3 gangliosides by engineered *E. coli*," Chem. Commun., 2005, vol. 20, pp. 2558-2560.

Hägg, P., et al., "A host/plasmid system that is not dependent on antibiotics and antibiotic resistance genes for stable plasmid maintenance in *Escherichia coli*," Journal of Biotechnology, 2004, vol. 111, pp. 17-30.

Joyce, A.R., et al., "Experimental and Computational Assessment of Conditionally Essential Genes in *Escherichia coli*," Journal of Bacteriology, 2006, vol. 188(23), pp. 8259-8271.

Priem, B., et al., "A new fermentation process allows large-scale production of human milk oligosaccharides by metabolically engineered bacteria,"Glycobiology, 2002, vol. 12(4), pp. 235-240.

Urashima, T. et al. (2011) Nutrition and Diet Research Progress: Milk Oligosaccharides. New York: Nova Science Publishers, Inc. 92 pages.

(Continued)

*Primary Examiner* — Kagnew H Gebreyesus
(74) *Attorney, Agent, or Firm* — Neal, Gerber & Eisenberg LLP

(57) ABSTRACT

The invention relates to a microbial production of recombinant oligosaccharides, particularly of human milk oligosaccharides (HMOs), using a genetically modified microorganism, particularly *E. coli*, in antibiotic-free cultivating medium.

19 Claims, No Drawings

(56) References Cited

OTHER PUBLICATIONS

Varki A, Cummings RD, Esko JD, et al., editors. "Chapter 4 Glycosylation Precursors." Essentials of Glycobiology. 2nd edition. Cold Spring Harbor (NY): Cold Spring Harbor Laboratory Press; 2009.

Velur Selvamani, R.S., et al., "Antibiotic-free segregational plasmid stabilization in *Escherichia coli* owing to the knockout of triosephosphate isomerase (tpiA)," Microbial Cell Factories, 2014, vol. 13:58, 13 pages.

Vidal, L., et al., "Development of an antibiotic-free plasmid selection system based on glycine auxotrophy for recombinant protein overproduction in *Escherichia coli*," Journal of Biotechnology, 2008, vol. 134, pp. 127-136.

FERMENTATIVE PRODUCTION OF OLIGOSACCHARIDES

CROSS-REFERENCE TO RELATED APPLICATION

This application is a national stage entry pursuant to 35 U.S.C. § 371 of International Application No. PCT/DK2016/050447, filed on Dec. 19, 2016, which claims priority to Denmark Patent Application No. PA 2015 70834, filed on Dec. 18, 2015, the contents of all of which are fully incorporated herein by reference.

FIELD OF THE INVENTION

The present invention relates to the field of biotechnology, notably to a microbial production of recombinant oligosaccharides, particularly of human milk oligosaccharides (HMOs), using a genetically modified microorganism, particularly E. coli, in antibiotic-free cultivating medium.

BACKGROUND OF THE INVENTION

The fermentative syntheses of foreign or exogenous oligosaccharides using recombinant microorganisms have recently become of great commercial and industrial interest. In such syntheses, oligosaccharides of interest would be synthesized by enzymatic glycosylation of sugar acceptors mediated by one or more heterologous glycosyl transferases of the microorganisms, and the one or more activated sugar nucleotides necessary for glycosylation would be produced by the same microorganism through overexpressing one or more genes encoding endogenous activated sugar nucleotide producing enzymes. As the microorganisms have been genetically manipulated, antibiotic-resistance selection marker genes have been utilized to separate the transformed microorganisms from the non-transformed ones in the inoculum and the fermentation broth (see e.g. WO 01/04341, Priem et al. *Glycobiology* 12, 235 (2002), Fort et al. *Chem. Comm.* 2558 (2005), Drouillard et al. *Angew. Chem. Int. Ed.* 45, 1778 (2006), WO 2010/070104, WO 2013/182206, WO 2014/048439). However, the use of antibiotics has been avoided in making HMOs by integrating the recombinant genes coding for enzymes involved in the de novo biosynthesis of the donor sugar and those coding for the necessary glycosyl transferases in the chromosome of the microorganisms (Baumgärtner et al. *Microb. Cell Fact.* 12:40 (2013), *ChemBioChem* 15, 1896 (2014)).

Dong et al. *Appl. Environ. Microbiol.* 76, 2295 (2010) disclosed a plasmid selection system based on complementation of host auxotrophy to construct a non-antibiotic system that can be applied in DNA vaccine and gene therapy.

There has been, however, a continuing need for alternative transformed microorganisms for making recombinant oligosaccharides, particularly HMOs, that are productive, can be easily constructed and does not require antibiotic selection.

SUMMARY OF THE INVENTION

The first aspect of the invention is a genetically modified cell for the production of an oligosaccharide comprising
  a recombinant gene encoding a glycosyl transferase necessary for the synthesis of said oligosaccharide,
  a biosynthetic pathway to produce a monosaccharide nucleotide donor suitable to be transferred by said glycosyl transferase to an acceptor,
  a chromosomal (native) gene essential for the growth of said cell, which gene is substantially inactivated or deleted, and
  an expression plasmid comprising
    said chromosomal gene, or
    a DNA sequence encoding the product of said chromosomal gene that is essential for the growth of said cell, DNA sequence(s) necessary for the expression of said DNA coding sequence.

Preferably, the oligosaccharide produced by the cell of this invention is of 3-8, more preferably of 3-5 monosaccharide units. Also preferably, the oligosaccharide is an HMO, more preferably an HMO of 3-8 monosaccharide units, even more preferably an HMO of 3, 4 or 5 monosaccharide units.

The second aspect of the invention is a method for making a recombinant oligosaccharide, preferably a human milk oligosaccharide, more preferably a human milk oligosaccharide of 3-5 monosaccharide units, by glycosylating a carbohydrate acceptor which is preferably lactose, comprising the steps of:
  a) providing a cell of the first aspect of the invention,
  b) culturing said cell in the presence of said acceptor, and
  c) separating said oligosaccharide from said cell, from the culture medium or from both.

DETAILED DESCRIPTION OF THE INVENTION

The terms defined below are applicable to all embodiments of the invention unless otherwise specified.

The term "cell" in the present context designates any biological cell, e.g. any prokaryotic or eukaryotic cell, that can be genetically manipulated to express its native or foreign genes, being as chromosome (chromosomal) gene or plasmid integrated (plasmid-borne) gene, at different expression levels, e.g. in one embodiment, expression of a gene in cell may be down-regulated by inactivation of said gene, e.g. via introduction a mutation into the gene DNA sequence, or via deletion of the gene sequence from the genome partially or entirely. The term "substantially" in relation to inactivation or deletion of gene sequence in the present context means that a cell comprising such inactivated or deleted gene expresses significantly lower amounts of a product of said gene such as RNA sequence(s) or polypeptide(s) that are essential for the cell metabolism, or completely lacks said products of the gene. In one preferred embodiment, a cell is a bacterial cell, e.g. E. coli cell. The term "gene" means a locus (or region) of a DNA which is made up of nucleotides and is the molecular unit of heredity. In the present content the term "gene" typically refers to a nucleic acid sequence comprising (i) a DNA sequence encoding a molecule that has a function in cell physiology, e.g. a polypeptide such as an enzyme, structural protein, etc., and (ii) one or more sequences that regulate the expression of the DNA sequence (i), e.g. promoter or operator sequences.

The term "expression" when used in reference to a nucleic acid sequence, such as a gene, refers to the process of converting the genetic information encoded in a gene into an RNA (e.g. mRNA, rRNA, tRNA or snRNA) through "transcription" of the gene (i.e. via the enzymatic action of an RNA polymerase), and into a protein where applicable (when a gene encodes a protein), through "translation" of the mRNA. Gene expression can be regulated at many stages in the process. "Up-regulation" or "activation" refers to regulation that increases the production of the gene expression products (i.e. RNA or protein), while "down-regulation" or "repression" refers to regulation that decrease production. Molecules (e.g. transcription factors) that are involved in up-regulation or down-regulation are often called "activators" and "repressors," respectively.

The term "DNA sequence necessary for expression of a DNA coding sequence" means a gene expression regulatory sequence, such as a promoter, operator or alike.

The term "recombinant DNA" designates DNA molecules formed by laboratory methods of genetic recombination (such as molecular cloning) to bring together genetic material from multiple sources, creating sequences that would not otherwise be found in the genome. The term "recombinant gene" means a gene comprising a recombinant DNA sequence. The term "recombinant cell" relates to a biological cell comprising a recombinant DNA molecule or recombinant gene.

The term "plasmid" means is a small DNA molecule within a cell that is physically separated from a chromosomal DNA and can replicate independently. "Expression plasmid" means in the present context a plasmid designed for gene expression in a cell of the invention. The expression plasmid is used to introduce a specific gene, e.g. a selection marker gene, into a target cell, and can commandeer the cell's mechanism for protein synthesis to produce the protein encoded by the gene.

The term "gene that is essential for the growth of the cell" or "essential gene" preferably means a natural gene of the cell without which the cell is unable to grow and consequently cannot survive. The essential gene is preferably involved in the synthesis of DNA precursors, amino acids or the cell wall, and encodes a product or a component which is necessary for the synthesis of DNA precursors, amino acids or the cell wall. If the cell is cultured in a minimal medium, that is a medium not containing necessary precursor(s) from which the cell might be able to produce the missing essential component in the salvage pathway anyway, the cell eventually dies. However, a plasmid-borne copy of the substantially deleted or inactivated essential gene, or at least DNA sequence(s) of the substantially deleted or inactivated essential gene necessary to express the product of said essential gene makes the cell alive because it complements the missing chromosomal (native) gene as a selection marker. Examples of such essential chromosomal (native) genes are dapD, infA, glyA or nadC. Functional equivalents of the essential genes of the invention, e.g. an orthologue gene (i.e. a gene in different species that is evolved from a common ancestral gene by speciation) that has the same function as the deleted/inactivated essential gene of the invention, are included in the scope as well.

The term "wild-type" or "native", when made in reference to a gene, refers to a functional gene common throughout an outbred population. As used herein, the term "wild-type" or "native", when made in reference to a gene product, refers to a functional gene product common throughout an outbred population. A functional wild-type gene is that which is most frequently observed in a population and is thus arbitrarily designated the "normal" or "native" or "wild-type" form of the gene.

As used herein, the term "modified" or "mutant", when made in reference to a gene or to a gene product, refers, respectively, to a gene or to a gene product which displays modifications in the sequence and/or functional properties (i.e. altered characteristics) when compared to the wild-type gene or gene product. Thus, the terms "variant" and "mutant", when used in reference to a nucleotide sequence, refer to a nucleic acid sequence that differs by one or more nucleotides from another, usually related nucleotide acid sequence. A "variation" is a difference between two different nucleotide sequences; typically, one sequence is a reference sequence.

The term "selection marker" refers to a gene which encodes an enzyme having an activity that confers resistance to an antibiotic ("antibiotic marker") or a drug upon the cell in which the selectable marker is expressed ("drug marker"), or which confers expression of a trait which can be detected (e.g. luminescence or fluorescence), or a protein that is essential for the growth of the cell. Selectable markers may be "positive" or "negative." Examples of positive selectable markers include the neomycin phosphotrasferase (NPTII) gene that confers resistance to G418 and to kanamycin, and the bacterial hygromycin phosphotransferase gene (hyg), which confers resistance to the antibiotic hygromycin. Negative selectable markers encode an enzymatic activity whose expression is cytotoxic to the cell when grown in an appropriate selective medium. For example, the HSV-tk gene is commonly used as a negative selectable marker. Expression of the HSV-tk gene in cells grown in the presence of gancyclovir or acyclovir is cytotoxic; thus, growth of cells in selective medium containing gancyclovir or acyclovir selects against cells capable of expressing a functional HSV TK enzyme. In one preferred embodiment, the invention relates to an essential gene as defined above as a selection marker, e.g. dapD, infA, glyA or nadC.

In accordance with this invention, the term "genetically modified cell" or "genetically modified microorganism" preferably means a cell of a microorganism, especially an *E. coli* cell, in which there is at least one alteration in its DNA sequence. The alteration can result in a change in the original characteristics of the wild type cell, e.g. the modified cell is able to perform additional chemical transformation due to the introduced new genetic material that encodes the expression of an enzymes not being in the wild type cell, or is not able to carry out transformation like degradation due to removal of gene/genes (knockout). A genetically modified cell can be produced in a conventional manner by genetic engineering techniques that are well-known to those skilled in the art.

In this invention, the term "monosaccharide" preferably means a sugar of 5-9 carbon atoms that is an aldose (e.g. D-glucose, D-galactose, D-mannose, D-ribose, D-arabinose, L-arabinose, D-xylose, etc.), a ketose (e.g. D-fructose, D-sorbose, D-tagatose, etc.), a deoxysugar (e.g. L-rhamnose, L-fucose, etc.), a deoxy-aminosugar (e.g. N-acetylglucosamine, N-acetylmannosamine, N-acetylgalactosamine, etc.), an uronic acid, a ketoaldonic acid (e.g. sialic acid) or equivalents.

The term "oligosaccharide" preferably means a sugar polymer containing at least two monosaccharide units (vide supra). The oligosaccharide can have a linear or branched structure containing monosaccharide units that are linked to each other by interglycosidic linkage.

The term "recombinant oligosaccharide" preferably means an oligosaccharide made by a genetically modified (recombinant) microorganism.

The term "human milk oligosaccharide" or "HMO" preferably means a complex carbohydrate found in human breast milk (Urashima et al.: *Milk Oligosaccharides*. Nova Science Publishers, 2011). The HMOs have a core structure being a lactose unit at the reducing end that can be elongated by one or more β-N-acetyl-lactosaminyl and/or one or more β-lacto-N-biosyl units, and which core structures can be substituted by an α L-fucopyranosyl and/or an α-N-acetyl-neuraminyl (sialyl) moiety. In this regard, the non-acidic (or neutral) HMOs are devoid of a sialyl residue, and the acidic HMOs have at least one sialyl residue in their structure. The non-acidic (or neutral) HMOs can be fucosylated or non-fucosylated. Examples of such neutral non-fucosylated HMOs include lacto-N-triose (LNTri, GlcNAc(β1-3)Gal(β1-4)Glc), lacto-N-tetraose (LNT), lacto-N-neotetraose (LNnT), lacto-N-neohexaose (LNnH), para-lacto-N-neohexaose (pLNnH), para-lacto-N-hexaose (pLNH) and lacto-N-hexaose (LNH). Examples of neutral fucosylated HMOs include 2'-fucosyllactose (2'-FL), lacto-N-fucopentaose I (LNFP-I), lacto-N-difucohexaose I (LNDFH-I), 3-fucosyllactose (3-FL), difucosyllactose (DFL), lacto-N-fucopentaose II (LNFP-II), lacto-N-fucopentaose III (LNFP-III), lacto-N-difucohexaose III (LNDFH-III), fucosyl-lacto-N-hexaose II (FLNH-II), lacto-N-fucopentaose V (LNFP-V), lacto-N-difucohexaose II (LNDFH-II), fucosyl-lacto-N-hexaose I (FLNH-I), fucosyl-para-lacto-N-hexaose I (FpLNH-I), fucosyl-para-lacto-N-neohexaose II (F-pLNnH II) and fucosyl-lacto-N-neohexaose (FLNnH). Examples of acidic HMOs include 3'-sialyllactose (3'-SL), 6'-sialyllactose (6'-SL), 3-fucosyl-3'-sialyllactose (FSL), LST a, fucosyl-LST a (FLST a), LST b, fucosyl-LST b (FLST b), LST c, fucosyl-LST c (FLST c), sialyl-LNH (SLNH), sialyl-lacto-N-hexaose (SLNH), sialyl-lacto-N-neohexaose I (SLNH-I), sialyl-lacto-N-neohexaose II (SLNH-II) and disialyl-lacto-N-tetraose (DSLNT).

The term "a glycosyl transferase necessary for the synthesis of an oligosaccharide" preferably means a glycosyl transferase that is able to transfer intracellularly the glycosyl residue of an activated monosaccharide nucleotide to an appropriate acceptor molecule. In this regard a glycosylation of the acceptor molecule takes place. The gene or an equivalent DNA sequence thereof, that encodes the glycosyl transferase, can be introduced into the cell by known techniques, e.g. by integrating it into the chromosome of the cell or using an expression vector. The origin of the heterologous gene or nucleic acid sequence can be any animal (including human) or plant, eukaryotic cells such as those from *Saccharomyces cerevisae, Saccharomyces pombe, Candida albicans* and the like, prokaryotic cells such as those originated from *E. coli, Bacillus subtilis, Campylobacter pylori, Helicobacter pylori, Agrobacterium tumefaciens, Staphylococcus aureus, Thermophilus aquaticus, Azorhizobium caulinodans, Rhizobium leguminosarum, Rhizobium meliloti, Neisseria gonorrhoeae* and *Neisseria meningitis*, or virus. The glycosyl transferase encoded by the gene or equivalent DNA sequence can be a glucosyl transferase, galactosyl transferase, N-acetylglucosaminyl transferase, N-acetylgalactosaminyl transferase, glucuronosyl transferase, xylosyl transferase, mannosyl transferase, fucosyl transferase, sialyl transferase or the like. In a preferred embodiment, the glycosyl transferase is selected from the group consisting of β-1,3-N-acetylglucosaminyl transferase, β-1,3-galactosyl transferase, β-1,3-N-acetylgalactosaminyl transferase, β-1,3-glucuronosyl transferase, β-1,6-N-acetylglucosaminyl transferase, β-1,4-N-acetylgalactosaminyl transferase, β-1,4-galactosyl transferase, α-1,3-galactosyl transferase, α-1,4-galactosyl transferase, α-2,3-sialyltransferase, α-2,6-sialyl transferase, α-2,8-sialyl transferase, α-1,2-fucosyl transferase, α-1,3-fucosyl transferase and α-1,4-fucosyl transferase. More preferably, the glycosyl transferase is selected from the group of enzymes involved in making an HMO, that is β-1,3-N-acetylglucosaminyl transferase, β-1,6-N-acetylglucosaminyl transferase, β-1,3-galactosyl transferase, β-1,4-galactosyl transferase, α-2,3-sialyl transferase, α-2,6-sialyl transferase, α-1,2-fucosyl transferase, α-1,3-fucosyl transferase and α-1,4 fucosyl transferase. The genes encoding the above-mentioned transferases have been described in the literature.

The term "a biosynthetic pathway to produce a monosaccharide nucleotide donor" preferably means that the genetically modified cell is able to produce an activated sugar nucleotide (a phosphorylated monosaccharide residue attached to a nucleoside such as UDP, dTDP, CMP or GDP) by a metabolic pathway. The genetically modified cell can produce one or more activated sugar nucleotide by a de novo pathway. In this regard, an activated sugar nucleotide is made by the cell under the action of enzymes involved in the de novo biosynthetic pathway of that respective sugar nucleotide in a stepwise reaction sequence starting from a simple carbon source like glycerol, fructose or glucose (for a review for monosaccharide metabolism see e.g. H. H. Freeze and A. D. Elbein: *Glycosylation precursors* in: *Essentials of Glycobiology*, 2nd edition (Eds. A. Varki et al.), Cold Spring Harbour Laboratory Press (2009)). The enzymes involved in the de novo biosynthetic pathway of an activated sugar nucleotide can be naturally present in the cell or introduced into the cell by means of gene technology or recombinant DNA techniques, all of them are parts of the general knowledge of the skilled person. In addition, the genetically modified cell can utilize a salvaged monosaccharide for producing an activated sugar nucleotide. In the salvage pathway, monosaccharides derived from degraded oligosaccharides are phosphorylated by kinases and converted to nucleotide sugars by pyrophosphorylases. The enzymes involved in the activated sugar nucleotide biosynthesis can be heterologous or native of the cell used for genetic modification. Preferably, the following activated sugar nucleotides are involved in the glycosyl transfer: UDP-Glc, UDP-Gal, UDP-GlcNAc, UDP-GalNAc, UDP-glucuronic acid, UDP-Xyl, GDP-Man, GDP-Fuc and CMP-sialic acid, more preferably UDP-Gal, UDP-GlcNAc, GDP-Fuc and CMP-sialic acid. A specific glycosyl transferase enzyme accepts only a specific activated sugar nucleotide, e.g. a galactosyl transferase utilizes UDP-Gal, and so on.

The term "acceptor" preferably means a mono- or disaccharide that reacts with and therefore is glycosylated by a monosaccharide nucleotide donor under the action of an appropriate glycosyl transferase to form an oligosaccharide of interest. The oligosaccharide of interest can be the product of a single glycosylation step implying that one monosaccharide unit is added to the acceptor. In addition, the oligosaccharide of interest can be produced by more than one, typically two or three, glycosylation steps, which take place sequentially. Preferably, the acceptor is lactose.

1. Genetically Modified Cells Capable of Synthesizing HMOs

It has been surprisingly discovered that a carbohydrate acceptor can be glycosylated in a microorganism, and an exogenous oligosaccharide can be produced and separated, wherein the oligosaccharide-producing microorganism is not fully genome engineered, however can grow in the absence of antibiotics. The genetically modified strains of the invention are suitable to make an oligosaccharide product of interest, preferably an HMO, in higher titre and/or with less by-product formation compared to other oligosaccharide producing cells of the prior art that can be cultivated in an antibiotic-free milieu (e.g. fully genome engineered plasmid-free variants) or those comprising plasmid(s) preferably with antibiotic marker(s). Thereby an efficient, safe and easily up-scalable process for producing oligosaccharides can be obtained that even fulfils the more and more strict regulatory requirements with regard to the antibiotic-based production systems.

The invention therefore, in a first aspect, relates to a genetically modified cell for the production of an oligosaccharide comprising a recombinant gene encoding a glycosyl transferase necessary for the synthesis of said oligosaccharide, a biosynthetic pathway to produce a monosaccharide nucleotide donor suitable to be transferred by said glycosyl transferase to an acceptor, a chromosomal (native) gene essential for the growth of said cell, which gene is substantially inactivated or deleted, and an expression plasmid comprising
  said chromosomal gene, or
    a DNA sequence encoding the product of said chromosomal gene that is essential for the growth of said cell and DNA sequence(s) necessary for the expression of said DNA coding sequence.

Preferably, the oligosaccharide produced by the cell of this invention is of 3-8, more preferably of 3-5 monosaccharide units. Also preferably, the oligosaccharide is an HMO, more preferably an HMO of 3-8 monosaccharide units, even more preferably an HMO of 3, 4 or 5 monosaccharide units.

The genetically modified cell of the invention contains preferably only one expression plasmid which plasmid comprises the chromosomal (native) gene that previously has been deleted from or inactivated in the chromosome and is essential for the growth of the cell, or a DNA sequence encoding the product of said chromosomal gene and DNA sequence(s) necessary for the expression of said DNA coding sequence, and at least one recombinant gene selected from
  the group of genes encoding a glycosyl transferase necessary for the synthesis of the oligosaccharide product or
  genes that express enzymes necessary to produce a monosaccharide nucleotide donor in a biosynthetic pathway, and which monosaccharide nucleotide donor is utilized in the synthesis of the oligosaccharide product.

Although the selection of the transfected cells is achieved by the complementation of the essential gene, the plasmid can comprise, mainly due to technical reasons, antibiotic marker left in the plasmid from earlier variants in the course of the metabolic engineering of the cell. This antibiotic marker optionally present, however, has no function in the fermentation process. In accordance with another preferred embodiment the plasmid expressing the essential gene which is deleted from or inactivated in the chromosome is void of an antibiotic marker.

In a preferred embodiment, the genetically modified cell has a substantially deleted or inactivated nadC gene in its chromosome and comprise a plasmid expressing nadC. The nadC gene is the part of the NAD biosynthesis pathway starting from L-aspartate and encodes the quinolinate phosphoribosyltransferase enzyme which makes nicotinic acid mononucleotide from quinolinic acid. The cell can be cultured in a medium not containing salvage pathway NAD precursors such as nicotinic acid, nicotinamide or nicotinamide riboside.

To delete or inactivate the nadC gene at least part of the coding sequence shall be deleted or interrupted, however other region(s) of the gene such us the promoter sequence, the upstream and/or the downstream of the open reading frame can also be deleted. It is required that at least the promoter region and the coding sequence, as DNA regions of the chromosomal nadC gene encoding and expressing the NadC enzyme as its product, are copied in the plasmid in order that the NadC enzyme is functionally expressed. The native promoter can be substituted by any suitable equivalent DNA sequence that is able to initiate the transcription of nadC in the plasmid. However, in one preferred embodiment, the whole locus including the upstream and the downstream is inserted in the plasmid to ensure that gene regulatory events are not defected.

Yet in a preferred embodiment, the cell comprises the recombinant gene encoding a glycosyl transferase necessary for the synthesis of the oligosaccharide of interest in a plasmid, preferably in the same plasmid that comprise the essential gene (e.g. nadC) which is deleted from or inactivated in the chromosome or comprise a DNA sequence encoding the product of said chromosomal gene and DNA sequence(s) necessary for the expression of said DNA coding sequence. This embodiment is particularly preferred when the oligosaccharide product is a trisaccharide and the biosynthesis of monosaccharide nucleotide donor which is necessary for its production does not require exogenous gene(s), e.g. 2'-FL or 3-FL for the synthesis of which GDP-Fuc is produced by the cell's own natural metabolism. Likewise, this embodiment is also particularly preferred when the oligosaccharide product is at least a tetrasaccharide and at least two different recombinant glycosyl transferases are involved in its synthesis. Typically, one of the at least two recombinant glycosyl transferases is plasmid-borne.

Yet in a preferred embodiment, the cell has the recombinant gene encoding a glycosyl transferase necessary for the synthesis of the oligosaccharide of interest integrated in its chromosome. This embodiment is particularly preferred when the oligosaccharide product is a trisaccharide and the biosynthesis of monosaccharide nucleotide donor which is necessary for its production requires exogenous gene(s). In this case that/those recombinant gene(s) are comprised in a plasmid, preferably in the same plasmid carrying the essential gene (e.g. nadC) which is deleted from or inactivated in the chromosome or carrying a DNA sequence encoding the product of said chromosomal gene and DNA sequence(s) necessary for the expression of said DNA coding sequence, and the recombinant glycosyl transferase is chromosomally integrated, as e.g. in a 3'-SL or 6'-SL producing strain.

The genetically modified cell of the first aspect described above is able to internalize an exogenously added acceptor from the culture medium into the cell where it is glycosylated to produce the oligosaccharide of interest. The internalization of the acceptor should not, of course, affect the basic and vital functions or destroy the integrity of the cell. In one embodiment the internalization can take place via a passive transport mechanism during which the exogenous acceptor diffuses passively across the plasma membrane of the cell. The flow is directed by the concentration difference in the extra- and intracellular space with respect to the acceptor molecule to be internalized, which acceptor is supposed to pass from the place of higher concentration to the zone of lower concentration tending towards equilibrium. In other embodiment the exogenous acceptor can be internalized in the cell with the aid of an active transport mechanism, during which the exogenous acceptor diffuses across the plasma membrane of the cell under the influence of a transporter protein or permease of the cell. Lactose permease (LacY) has specificity towards mono- or disaccharide selected from galactose, N-acetyl-glucosamine, a galactosylated monosaccharide (such as lactose), an N-acetyl-glucosaminylated monosaccharide and glycosidic derivatives thereof. All these carbohydrate derivatives can be easily taken up by a cell having a LacY permease by means of an active transport and accumulate in the cell before being glycosylated (WO 01/04341, Fort et al. *J. Chem. Soc., Chem. Comm.* 2558 (2005), EP-A-1911850, WO 2013/182206, WO 2014/048439). This is because the cell is able to transport these carbohydrate acceptors into the cell using its LacY permease, and the cell lacks any enzymes that could degrade these acceptors, especially LacZ. The specificity towards the sugar moiety of the substrate to be internalized can be altered by mutation by means of known recombinant DNA techniques. In a preferred embodiment, the exogenously added acceptor is lactose, and its internalization takes place via an active transport mechanism mediated by a lactose permease of the cell, more preferably LacY. This type of cell thus produces oligosaccharides which has a lactose moiety at their reducing end, preferably human milk oligosaccharides. Also preferably, the cell has a deleted or deficient lacA gene on the lac operon.

Yet in a preferred embodiment, the genetically modified cell comprises at least one gene that encodes a glycosyl transferase selected from the group consisting of β-1,3-N-acetylglucosaminyl transferase, β-1,6-N-acetylglucosaminyl transferase, β-1,3-galactosyl transferase, β-1,4-galactosyl transferase, α-2,3-sialyltransferase, α-2,6-sialyl transferase, α-1,2-fucosyl transferase, α-1,3-fucosyl transferase and α-1,4 fucosyl transferase. By applying the proper selection of the glycosyl transferases the cell is suitable for making HMOs using lactose as acceptor, by whatever means the lactose is internalized by the cell. For example to make a trisaccharide HMO one glycosyl transferase is necessary, the utilization of an α-2,3-sialyl transferase, an α-2,6-sialyl transferase, an α-1,2-fucosyl transferase or an α-1,3-fucosyl transferase produces 3'-SL, 6'-SL, 2'-FL or 3-FL, respectively. In case of making a tetrasaccharide or a higher HMO the proper combination of selected glycosyl transferases leads to the desired HMO due to the substrate selectivity of a given glycosyl transferase. For example LNnT can be produced when a β-1,3-N-acetylglucosaminyl transferase and a β-1,4-galactosyl transferase are simultaneously expressed by the cell. The lactose acceptor is first N-acetylglucosaminylated to make lacto-N-triose because the β-1,3-N-acetylglucosaminyl transferase has high affinity towards lactose while the β-1,4-galactosyl transferase has not or lower. The intermediate lacto-N-triose is subsequently galactosylated to give LNnT because it is a better substrate for the β-1,4-galactosyl transferase.

Yet in a preferred embodiment, the genetically modified cell comprises a biosynthetic pathway, preferably a de novo pathway, to produce at least one of UDP-Gal, UDP-GlcNAc, GDP-Fuc or CMP-sialic acid, the monosaccharide nucleotide donors suitable to be transferred by the corresponding glycosyl transferases listed above that convert lactose to the desired HMOs. More preferably, the genetically modified cell produces UDP-Gal, UDP-GlcNAc and/or GDP-Fuc using its indigenous genes, for example *E. coli* strains do so. As to the production of CMP-sialic acid, however, heterologous expression of genes are required, preferably from a plasmid, more preferably by the same plasmid that carries the essential gene which is deleted from or inactivated in the chromosome. In one way of producing CMP-sialic acid in the cell, exogenously added sialic acid is internalized actively or passively, preferably actively by a sialic acid permease, more preferably by that encoded by nanT, and subsequently converted to CMP-sialic acid by a CMP-NeuAc synthase, e.g. encoded by a heterologous neuA. In another way the internally available UDP-GlcNAc is utilized, by expressing neuC, neuB and neuA that convert it to CMP-sialic acid via ManNAc and sialic acid as intermediates.

The genetically modified cell of the first aspect, including the preferred and the more preferred embodiments, lacks enzymes that likely break or degrade the oligosaccharide product, the monosaccharide nucleotide donor, the acceptor and/or any precursors thereof. The genes expressing these enzymes can be deleted or inactivated by the methods known in the art. In this regard the genetically engineered cell, if lactose is used as acceptor, has a phenotype of LacZ$^-$ and/or LacA$^-$, that is it lacks a β-galactosidase and/or transacetylase activity/activities that would degrade and/or acetylate lactose, respectively. With regard to CMP-sialic acid biosynthesis, the cell's catabolic activity on sialic acid and its precursor is suppressed by inactivating/deletion of the aldolase gene (nanA) and/or the ManNAc kinase gene (nanK).

The genetically modified cell of the first aspect, including the preferred and the more preferred embodiments, can have a sugar efflux transporter that promotes the effluence of the oligosaccharide produced from the cell to the supernatant. The sugar efflux transporter can be present exogenously or endogenously and is overexpressed under the conditions of the fermentation to enhance the export of the oligosaccharide. The specificity towards the sugar moiety of the product to be secreted can be altered by mutation by means of known recombinant DNA techniques.

1.1 Genetically Modified Cells Capable of Synthesizing Non-Acidic HMOs

In an embodiment of the first aspect, the genetically modified cell is able to produce a non-acidic (neutral) HMO. In this regard the cell comprises gene(s) expressing a β-1,3-N-acetylglucosaminyl transferase, a β-1,6-N-acetylglucosaminyl transferase, a β-1,3-galactosyl transferase, a β-1,4-galactosyl transferase, an α-1,2-fucosyl transferase, an α-1,3-fucosyl transferase and/or an α-1,4 fucosyl transferase, a biosynthetic pathway to produce UDP-Gal, UDP-GlcNAc and/or GDP-Fuc, a substantially deleted or inactivated chromosomal nadC gene, a plasmid comprising nadC, or a DNA sequence encoding the NadC enzyme and DNA sequence(s) necessary for the expression of said DNA coding sequence, and preferably a functional lactose permease, more preferably LacY.

1.1.1 Genetically Modified Cells Capable of Synthesizing Non-Acidic and Non-Fucosylated HMOs Preferably, the non-acidic HMO is devoid of fucosyl residue can be e.g. LNTri, LNT, LNnT, LNH, LNnH, pLNH or pLNnH; in this regard the cell comprises recombinant gene(s) expressing β-1,3-N-acetylglucosaminyl transferase, β-1,6-N-acetylglucosaminyl transferase, β-1,3-galactosyl transferase and/or β-1,4-galactosyl transferase. More preferably, the HMO devoid of sialyl and fucosyl residue is a trisaccharide, that is LNTri, or a tetrasaccharide, that is LNT or LNnT.

Specifically, the genetically modified microorganism or cell of the invention is able to produce primarily, preferably substantially exclusively, LNTri. In this regard the cell comprises a gene expressing a β-1,3-N-acetylglucosaminyl transferase, a biosynthetic pathway to produce UDP-GlcNAc, a substantially deleted or inactivated chromosomal nadC gene, a plasmid comprising nadC or a DNA sequence encoding the NadC enzyme and DNA sequence(s) necessary for the expression of said DNA coding sequence, and preferably a functional lactose permease, more preferably LacY.

The above LNTri producing cell preferably contains only a single recombinant glycosyl transferase, a β-1,3-N-acetylglucosaminyl transferase, in order to minimize concurrent glycosylation steps leading to glycosylated trisaccharides different than LNTri and/or elongated variants such as tetra-, pentasaccharides, etc. The β-1,3-N-acetylglucosaminyl transferase has a strong affinity towards lactose; LNTri, however, is an unfavourable substrate for a β-1,3-N-acetylglucosaminyl transferase, thus further glycosylation on the product is unlikely to occur. In this LNTri producing cell the recombinant gene encoding the β-1,3-N-acetylglucosaminyl transferase can be integrated in the chromosome or can be comprised by a plasmid, preferably the same plasmid that comprises nadC or a DNA sequence encoding the NadC enzyme and DNA sequence(s) necessary for the expression of said DNA coding sequence. More preferably, said plasmid further comprises a native LacY.

Also specifically, the genetically modified microorganism or cell of the invention is able to produce primarily, preferably substantially exclusively, LNT. In this regard the cell comprises a gene expressing a β-1,3-N-acetylglucosaminyl transferase, a gene expressing a β-1,3-galactosyl transferase, a biosynthetic pathway to produce UDP-GlcNAc and UDP-Gal, a substantially deleted or inactivated chromosomal nadC gene, a plasmid comprising nadC or a DNA sequence encoding the NadC enzyme and DNA sequence(s) necessary for the expression of said DNA coding sequence, and preferably a functional lactose permease, more preferably LacY.

The above LNT producing cell preferably contains only two recombinant glycosyl transferases, a β-1,3-N-acetylglucosaminyl transferase and a β-1,3-galactosyl transferase, in order to minimize concurrent glycosylation steps leading to unwanted by-products. This cell therefore performs two distinct glycosylation steps. The β-1,3-N-acetylglucosaminyl transferase has a strong affinity towards lactose whereas the β-1,3-galactosyl transferase has not or lower, therefore LNTri is expected to be made first. LNTri is, however, an unfavourable substrate for a β-1,3-N-acetylglucosaminyl transferase but the β-1,3-galactosyl transferase accepts it easily, thus in a second glycosylation step (galactosylation) LNT is readily produced. In this LNT producing cell the recombinant genes encoding the β-1,3-N-acetylglucosaminyl transferase and the β-1,3-galactosyl transferase can be integrated in the chromosome or can be comprised by a plasmid, preferably the same plasmid that comprises nadC or a DNA sequence encoding the NadC enzyme and DNA sequence(s) necessary for the expression of said DNA coding sequence. Said plasmid may further comprise native LacY. Even more preferably, one of the genes encoding the β-1,3-N-acetylglucosaminyl transferase and the β-1,3-galactosyl transferase is chromosomally integrated and the other is the part of the above plasmid. In a particularly preferred embodiment the β-1,3-N-acetylglucosaminyl transferase is chromosomally integrated and the β-1,3-galactosyl transferase is plasmid-borne.

Yet specifically, the genetically modified microorganism or cell of the invention is able to produce primarily, preferably substantially exclusively, LNnT. In this regard the cell comprises a gene expressing a β-1,3-N-acetylglucosaminyl transferase, a gene expressing a β-1,4-galactosyl transferase, a biosynthetic pathway to produce UDP-GlcNAc and UDP-Gal, a substantially deleted or inactivated chromosomal nadC gene, a plasmid comprising nadC or a DNA sequence encoding the NadC enzyme and DNA sequence(s) necessary for the expression of said DNA coding sequence, and preferably a functional lactose permease, more preferably LacY.

The above LNnT producing cell preferably contains only two recombinant glycosyl transferases, a β-1,3-N-acetylglucosaminyl transferase and a β-1,4-galactosyl transferase, in order to minimize concurrent glycosylation steps leading to unwanted by-products. This cell therefore performs two distinct glycosylation steps. The β-1,3-N-acetylglucosaminyl transferase has a strong affinity towards lactose whereas the β-1,4-galactosyl transferase has not or lower, therefore LNTri is expected to be made first. LNTri is, however, an unfavourable substrate for a β-1,3-N-acetylglucosaminyl transferase but the β-1,4-galactosyl transferase accepts it easily, thus in a second glycosylation step (galactosylation) LNnT is readily produced. Preferably, in this LNnT producing cell the recombinant genes encoding the β-1,3-N-acetylglucosaminyl transferase and the β-1,4-galactosyl transferase can be integrated in the chromosome or can be comprised by a plasmid, preferably the same plasmid that comprises nadC or a DNA sequence encoding the NadC enzyme and DNA sequence(s) necessary for the expression of said DNA coding sequence. More preferably, said plasmid further comprises native LacY. Even more preferably, one of the genes encoding the β-1,3-N-acetylglucosaminyl transferase and the β-1,4-galactosyl transferase is chromosomally integrated and the other is the part of the above plasmid. In a particularly preferred embodiment the chromosomal is chromosomally integrated and the β-1,4-galactosyl transferase is plasmid-borne.

The claimed strains having a plasmid carrying the essential gene deleted or inactivated from the strain's chromosome, preferably nadC, for the synthesis of tetrasaccharides like LNT or LNnT show reduced by-product ratios compared to either fully chromosomal or antibiotic marker carrying plasmid strain variants known or anticipated by the prior art. Furthermore, the one-plasmid nadC variants provide higher product titre than the 2-plasmid strains containing 2 antibiotic markers.

1.1.2 Genetically Modified Cells Capable of Synthesizing Fucosylated Non-Acidic HMOs According to another embodiment the genetically modified cell of the invention is capable of synthesizing non-acidic HMOs that comprises at least one fucose residue. The fucose containing non-acidic (neutral) HMO is preferably a mono- or difucosylated lactose, LNT or LNnT.

Surprisingly, the claimed strains having a plasmid carrying the essential gene deleted or inactivated from the strain's chromosome, preferably nadC, for the synthesis of fucosylated non-acidic HMOs show better productivity compared to either fully chromosomal or antibiotic marker carrying plasmid strain variants known or anticipated by the prior art, wherein the expression level of the recombinant fucosyl transferase and that of the indigenous enzymes involved in the GDP-Fuc biosynthesis is comparable.

1.1.2.1 Genetically Modified Cells Capable of Synthesizing Neutral Fucosylated Lactoses (2'-FL, 3-FL, DFL)

Specifically, the genetically modified microorganism or cell of the invention is able to produce primarily, preferably substantially exclusively, 2'-FL. In this regard the cell comprises a gene expressing an α-1,2-fucosyl transferase,
a biosynthetic pathway to produce GDP-Fuc,
a substantially deleted or inactivated chromosomal nadC gene,
a plasmid comprising nadC or a DNA sequence encoding the NadC enzyme and DNA sequence(s) necessary for the expression of said DNA coding sequence, and
preferably a functional lactose permease, more preferably LacY.

The above 2'-FL producing cell preferably contains only a single recombinant glycosyl transferase, notably an α-1,2-fucosyl transferase, in order to minimize concurrent glycosylation steps leading to glycosylated trisaccharides different than 2'-FL and/or elongated variants such overfucosylated by-products. In this 2'-FL producing cell the recombinant gene encoding the α-1,2-fucosyl transferase can be integrated in the chromosome or can be comprised by a plasmid, preferably the same plasmid that comprises nadC or a DNA sequence encoding the NadC enzyme and DNA sequence(s) necessary for the expression of said DNA coding sequence. More preferably, said plasmid further comprises a native LacY.

Also specifically, the genetically modified microorganism or cell of the invention is able to produce primarily, preferably substantially exclusively, 3-FL. In this regard the cell comprises a gene expressing an α-1,3-fucosyl transferase,
a biosynthetic pathway to produce GDP-Fuc,
a substantially deleted or inactivated chromosomal nadC gene,
a plasmid comprising nadC or a DNA sequence encoding the NadC enzyme and DNA sequence(s) necessary for the expression of said DNA coding sequence, and
preferably a functional lactose permease, more preferably LacY.

The above 3-FL producing cell preferably contains only a single recombinant glycosyl transferase, an α-1,3-fucosyl transferase, in order to minimize concurrent glycosylation steps leading to glycosylated trisaccharides different than 3-FL and/or elongated variants such overfucosylated by-products. In this 3-FL producing cell the recombinant gene encoding the α-1,3-fucosyl transferase can be integrated in the chromosome or can be comprised by a plasmid, preferably the same plasmid that comprises nadC or a DNA sequence encoding the NadC enzyme and DNA sequence(s) necessary for the expression of said DNA coding sequence. More preferably, said plasmid further comprises a native LacY.

Yet specifically, the genetically modified microorganism or cell of the invention is able to produce primarily, preferably substantially exclusively, DFL. In this regard the cell comprises a gene expressing an α-1,2-fucosyl transferase,
a gene expressing an α-1,3-fucosyl transferase,
a biosynthetic pathway to produce GDP-Fuc,
a substantially deleted or inactivated chromosomal nadC gene,
a plasmid comprising nadC or a DNA sequence encoding the NadC enzyme and DNA sequence(s) necessary for the expression of said DNA coding sequence, and
preferably a functional lactose permease, more preferably LacY.

The above DFL producing cell preferably contains only two recombinant glycosyl transferases, an α-1,2-fucosyl transferase and an α-1,3-fucosyl transferase, in order to minimize concurrent glycosylation steps leading to unwanted by-products. This cell therefore performs two distinct glycosylation steps. Both the α-1,2-fucosyl transferase and the α-1,3-fucosyl transferase have a strong affinity towards lactose, therefore a mixture of 2'-FL and 3-FL is expected to be made first. In a second glycosylation step the α-1,2-fucosyl transferase fucosylates the intermediary 3-FL and similarly the α-1,3-fucosyl transferase fucosylates the intermediary 2'-FL thus DFL is readily produced. Preferably, in this DFL producing cell the recombinant genes encoding the α-1,2-fucosyl transferase and the α-1,3-fucosyl transferase can be integrated in the chromosome or can be comprised by a plasmid, preferably the same plasmid that comprises nadC or a DNA sequence encoding the NadC enzyme and DNA sequence(s) necessary for the expression of said DNA coding sequence. More preferably, said plasmid further comprises native LacY. Even more preferably, one of the genes encoding the α-1,2-fucosyl transferase and the α-1,3-fucosyl transferase is chromosomally integrated and the other is the part of the above plasmid.

1.1.2.2 Genetically Modified Cells Capable of Synthesizing Neutral Fucosylated LNT or LNnT Another preferred embodiment of genetically modified cells capable of synthesizing fucosylated non-acidic HMOs is that which produces a neutral (non-acidic) fucosylated LNT or LNnT. In this regard the cell comprises a gene expressing a β-1,3-N-acetylglucosaminyl transferase,
a gene expressing a galactosyl transferase,
a gene expressing a fucosyl transferase,
a biosynthetic pathway to produce UDP-GlcNAc, UDP-Gal and GDP-Fuc,
a substantially deleted or inactivated chromosomal nadC gene,
a plasmid comprising nadC or a DNA sequence encoding the NadC enzyme and DNA sequence(s) necessary for the expression of said DNA coding sequence, and
preferably a functional lactose permease, more preferably LacY.

In the above cell the recombinant genes encoding the β-1,3-N-acetylglucosaminyl transferase the galactosyl transferase and the fucosyl transferase can be integrated in the chromosome or can be comprised by a plasmid, preferably the same plasmid that comprises nadC or a DNA sequence encoding the NadC enzyme and DNA sequence(s) necessary for the expression of said DNA coding sequence. More preferably, said plasmid further comprises native LacY. Even more preferably, one or two of the genes encoding the β-1,3-N-acetylglucosaminyl transferase, the galactosyl transferase and the fucosyl transferase is/are chromosomally integrated and the other(s) is/are the part of the above plasmid. Particularly, when the galactosyl transferase is a β-1,3-galactosyl transferase and the fucosyl transferase is an α-1,2-fucosyl transferase, then the cell is able to produce LNFP-I;
when the galactosyl transferase is a β-1,3-galactosyl transferase and the fucosyl transferase is an α-1,3/4- fucosyl transferase, then the cell is able to produce LNFP-II, LNFP-V and/or LNDFH-II;

when the galactosyl transferase is a β-1,4-galactosyl transferase and the fucosyl transferase is an α-1,3-fucosyl transferase, then the cell is able to produce LNFP-III and/or LNDFH-III;

when the galactosyl transferase is a β-1,3-galactosyl transferase and the fucosyl transferase is an α-1,2- and an α-1,4-fucosyl transferase, then the cell is able to produce LNDFH-I.

1.2 Genetically Modified Cells Capable of Synthesizing Acidic HMOs

In another embodiment of the first aspect, the genetically modified cell is able to produce an acidic (sialic acid containing) HMO. In this regard the cell comprises

- a gene expressing a sialyl transferase,
- a biosynthetic pathway to produce CMP-sialic acid,
- a substantially deleted or inactivated chromosomal nadC gene,
- a plasmid comprising nadC or a DNA sequence encoding the NadC enzyme and DNA sequence(s) necessary for the expression of said DNA coding sequence, and
- preferably a functional lactose permease, more preferably LacY.

Although some microorganisms are able to make sialic acid or CMP-sialic acid in the de novo biosynthetic pathway, they are pathogenic and cannot be used in safe microbial fermentation processes which produce compounds/ingredients for pharmaceutical and/or nutritional purposes. Other bacteria, like *E. coli* K12, considered as safe in regulatory point of view, however, lack the endogenous machinery for making CMP-sialic acid. Therefore those cells have to be made capable of producing CMP-sialic acid. This is preferably done by using the cell natural UDP-GlcNAc pool from which CMP-sialic acid is accessible in three enzymatic steps: a UDP-GlcNAc 2-epimerase first makes ManNAc, then a sialic acid synthase produces sialic acid and a CMP-sialic acid synthetase transforms it to CMP-sialic acid. All three enzymes are supplied by heterologous gene expression introduced in the microorganism by genetic modification. In addition, the microorganism comprises a further heterologous gene that encodes a sialyl transferase to utilize the so-formed CMP-sialic acid in sialylation of the internalized lactose or other appropriate acceptor that is made from the internalized lactose by the microorganism. In order to keep the CMP-sialic acid concentration sufficient and/or optimal for sialylation, the microorganism's native catabolic activity on sialic acid is inactivated by deletion, modification or inactivation of the endogenous sialic acid aldolase and ManNAc kinase.

In this regard the genetically modified cell for producing a sialic acid containing HMO comprises

- a gene expressing a sialyl transferase,
- a biosynthetic pathway to produce CMP-sialic acid comprising the genes encoding a UDP-GlcNAc 2-epimerase, a sialic acid synthase and a CMP-sialic acid synthetase,
- a substantially deleted or inactivated chromosomal nadC gene,
- a plasmid comprising nadC or a DNA sequence encoding the NadC enzyme and DNA sequence(s) necessary for the expression of said DNA coding sequence,
- preferably a functional lactose permease, more preferably LacY, and
- preferably deleted or inactivated genes encoding sialic acid aldolase and ManNAc kinase.

Preferably, the gene encoding a UDP-GlcNAc 2-epimerase is neuC, the gene encoding a sialic acid synthase is neuB and the gene encoding a CMP-sialic acid synthetase is neuA. Also preferably, the gene encoding a sialic acid aldolase is nanA and the gene encoding a ManNAc kinase is nanK.

In a genetically modified cell capable of synthesizing acidic HMOs all four exogenous genes mentioned above may be chromosomally integrated, but preferably at least one of them is expressed from a plasmid, more preferably the same plasmid expressing nadC. Even more preferably, the genes encoding a UDP-GlcNAc 2-epimerase, a sialic acid synthase and a CMP-sialic acid synthetase are plasmid-borne, particularly the same plasmid containing nadC, and the gene encoding the sialyl transferase is chromosomally integrated.

Surprisingly, the claimed strains having a plasmid carrying the essential gene deleted or inactivated from the strain's chromosome, preferably nadC, for the synthesis of sialylated HMOs show better productivity compared to either fully chromosomal strains or strain variants containing plasmid with antibiotic marker known or anticipated by the prior art, even when the expression level of the recombinant sialyl transferase and that of the recombinant enzymes involved in the CMP-sialic acid biosynthesis is comparable.

1.2.1 Genetically Modified Cells Capable of Synthesizing Acidic Trisaccharide HMOs In a preferred embodiment the acidic HMO is a trisaccharide, particularly a sialylated lactose, specifically 3'-SL or 6'-SL. These cells therefore contain only one exogenous gene encoding a glycosyl transferase, namely an α-2,3-sialyl transferase (for making 3'-SL) or an α-2,6-sialyl transferase (for making 6'-SL).

1.2.2 Genetically Modified Cells Capable of Synthesizing Acidic Tetra- or Higher Oligosaccharide HMOs In another preferred embodiment, the cell is constructed so to be able to synthesize sialylated HMOs longer than a trisaccharide. In this regard the features of the genetically modified cell dedicated for making non-acidic (fucosylated or non-fucosylated) HMOs as disclosed under point 1.1 above and those for producing acidic HMOs as described under point 1.2 above are combined. For example, a genetically modified cell for producing FSL comprises

- a gene expressing an α-2,3-sialyl transferase,
- a gene expressing an α-1,3-fucosyl transferase,
- a biosynthetic pathway to produce CMP-sialic acid comprising the genes encoding a UDP-GlcNAc 2-epimerase, a sialic acid synthase and a CMP-sialic acid synthetase,
- a biosynthetic pathway to produce GDP-Fuc,
- a substantially deleted or inactivated chromosomal nadC gene,
- a plasmid comprising nadC or a DNA sequence encoding the NadC enzyme and DNA sequence(s) necessary for the expression of said DNA coding sequence,
- preferably a functional lactose permease, more preferably LacY, and - optionally deleted or inactivated genes encoding sialic acid aldolase and ManNAc kinase.

2. Method For Making Recombinant Oligosaccharides by Using Genetically Modified Cells A second aspect of the invention relates to a process for making a recombinant oligosaccharide by glycosylating a carbohydrate acceptor which is preferably lactose, comprising the steps of:

a) providing a cell, preferably an *E. coli* cell, that can internalize said acceptor into said cell and comprises a recombinant gene encoding a glycosyl transferase necessary for the synthesis of said oligosaccharide, a biosynthetic pathway to produce a monosaccharide nucleotide donor suitable to be transferred by said glycosyl transferase to an acceptor, a substantially deleted or inactivated chromosomal (native) gene that is essential for the growth of said cell, and a plasmid expressing said chromosomal gene, b) culturing said cell in the presence of said acceptor, and c) separating said oligosaccharide from said cell, from the culture medium or from both.

Preferably, the recombinant oligosaccharide which can be produced by this method of the invention is of 3-8, more preferably of 3-5 monosaccharide units. Also preferably, the recombinant oligosaccharide is an HMO, more preferably an HMO of 3-8 monosaccharide units, even more preferably an HMO of 3-5 monosaccharide units.

In step a) of the method the cells provided are those disclosed in the first aspect of the invention, including the preferred and more preferred embodiments.

In step b) of the method culturing or fermenting the genetically modified cell provided in step a) can be carried out in a conventional manner in, for example, aerated spinner or shaking culture, or, more preferably, in a fermenter. The genetically modified cell is cultured in the presence of a carbon-based substrate such as glycerol, glucose, glycogen, fructose, maltose, starch, cellulose, pectin, chitin, etc. Preferably, the cell culturing is performed on glycerol and/or glucose. The cell is preferably cultured in a minimal medium, that is a medium not containing necessary precursor(s) from which the cell might be able to produce the missing essential component in the salvage pathway.

During fermentation the exogenous substrate, preferably lactose, is internalized to and accumulated in the cell. The internalized substrate, acting as acceptor, participates in a glycosyl transferase induced glycosylation reaction, in which a glycosyl residue of an activated nucleotide donor is transferred so that the acceptor is glycosylated. Optionally, when more than one glycosyl transferase is expressed by the cell, additional glycosylation reactions can occur resulting in the formation of the target oligosaccharide which is a tetra- or higher oligosaccharide. Of course, the cell preferably lacks any enzyme activity which would degrade the acceptor, intermediates or the oligosaccharides produced in the cell.

Optionally, the process further comprises the addition of an inducer to the culture medium to induce the expression in the cell of enzyme(s) and/or of protein(s) involved in the transport of the acceptor and/or in the glycosylation of the internalized acceptor and/or in the biosynthesis of the activated sugar nucleotide donors. The inducer is preferably isopropyl β-D-thiogalactoside (IPTG). However, the use of inducer is not necessary if the cell is of LacI$^-$ phenotype.

According to a preferred embodiment of the method, the genetically modified cell, particularly a LacZ$^-$Y$^+$ E. coli cell, is cultured in an aqueous culture medium in the following phases:

(i) an exponential cell growth phase ensured by a carbon source, preferably glucose, then (ii) a feeding phase with the same or different carbon source as taken in step (i), preferably glycerol, which is added continuously ensuring a limited cell growth.

During the feeding phase, the exogenous carbohydrate acceptor, preferably lactose, to be internalized by and glycosylated in the cell, can be added to the culture medium at once, sequentially or continuously. The acceptor can be added in this second phase as a pure solid/liquid or in a form of a concentrated aqueous solution or suspension. The oligosaccharide production takes place in this second phase and can take several days. Preferably, this feeding phase is performed under conditions allowing the production of a culture with a high cell density. The inducer (if needed) is preferably added to the culture medium in the beginning of the feeding phase.

At the end of step b) the oligosaccharide product has accumulated both in the intra- and the extracellular matrix of the microorganism. The product is then preferably transported out of the cell to the supernatant in a passive way, i.e. it can diffuse outside across the cell membrane. This transport can be facilitated by one or more sugar efflux transporters in the cell, i.e. proteins that promote the effluence of sugar derivatives from the cell to the supernatant. The sugar efflux transporter(s) can be present exogenously or endogenously and can be overexpressed under the conditions of the fermentation to enhance the export of the oligosaccharide derivative produced. The specificity towards the sugar moiety of the product to be secreted can be altered by mutation of the cell by means of conventional recombinant DNA manipulation techniques. Preferably, the oligosaccharide accumulates in the extracellular matrix. Alternatively, the oligosaccharide can be transported out of the cell to the supernatant by disrupting the cell walls in a conventional manner.

In step c), the oligosaccharide product can then be separated in a conventional manner from the aqueous culture medium, in which it was made by the cell. Standard, well known techniques for recovery of oligosaccharides such as thin or thick layer chromatography, column chromatography, ion exchange chromatography or membrane filtration can be used. For separating HMOs from fermentation broth see e.g. WO 01/04341, WO 2007/101832, WO 2012/112777, WO 2015/150328, WO 2015/106943, WO 2015/049331, WO 2015/036138, WO 2015/032412 or WO 2015/032413.

As an illustration of step c), the oligosaccharide is first separated from the microorganism which produced it. This preferably involves clarifying the culture medium to remove suspended particulates and contaminants, particularly cells, cell components, insoluble metabolites and cell debris produced by culturing the genetically modified microorganism. In this step, the aqueous culture medium, which contains the oligosaccharide product, can be clarified in a conventional manner. Preferably, the culture medium is clarified by centrifugation and/or filtration. Then substantially all the proteins, as well as peptides, amino acids, RNA and DNA and any endotoxins and glycolipids that could interfere with the subsequent separation steps, is removed from the aqueous culture medium, preferably after it has been clarified. In this step, proteins and related impurities can be removed from the culture medium in a conventional manner. Preferably, proteins and related impurities are removed from the culture medium by ultrafiltration, tangential flow high-performance filtration, tangential flow ultrafiltration, affinity chromatography, ion exchange chromatography, hydrophobic interaction chromatography and/or gel filtration (i.e. size exclusion chromatography), particularly by chromatography, more particularly by ion exchange chromatography or hydrophobic interaction chromatography. With the exception of size exclusion chromatography, proteins and related impurities are retained by a chromatography medium or a selected membrane, while the oligosaccharide product remains in the aqueous culture medium. If desired, the oligosaccharide product in the aqueous culture medium can then be separated from sugar-like by-product(s) and from the culture medium, after proteins and related impurities have been removed from the culture medium. This can be suitably done by subjecting the culture medium to chromatographic separation. This separation can be carried out, in case of a neutral oligosaccharide product, in a chromatographic separation column, filled with a conventional acidic cationic ion exchange resin. The acidic cationic ion exchange resin can be in monovalent or divalent cationic form and is preferably in $H^+$, $K^+$, $Na^+$, $Mg^{2+}$ or $Ca^{2+}$ form, particularly $Ca^{2+}$. The chromatographic separation can be carried out in a conventional manner at a pH of the solution of 2 to 9. The eluent used in the chromatographic separation is preferably water, especially demineralized water, but aqueous salt solutions can also be used. Alcohols, such as ethanol, and aqueous alcohol mixtures can also be used. Alternatively, the oligosaccharide product can be crystallized out from the pretreated aqueous solution. The oligosaccharide product may also be isolated from its aqueous solution, after the desired purification steps, by spray-drying.

Whilst the invention has been described with reference to preferred embodiments, it will be appreciated that various modifications are possible within the scope of the invention.

EXAMPLES

Strains were screened in 24 deep well plates using a 2-day protocol. During the first 24 hours, cells were grown to high densities while in the next 24 hours cells were transferred to a medium that allowed induction of gene expression and product formation. Specifically, during day 1 fresh inoculums were prepared using a basal minimal medium supplemented with magnesium sulphate, thiamine, glucose and the appropriate antibiotic(s) if required so. After overnight incubation of the prepared cultures at 34° C. with a 700 rpm shaking, cells were transferred to a new basal minimal medium supplemented with magnesium sulphate, thiamine, glucose, glycerol (0.5%), lactose, IPTG (if applicable) and the appropriate antibiotic(s) if required so. After inoculation of the new medium, cells were shaken at 700 rpm at 28° C. for 24 hours. After denaturing and centrifuge the supernatants were analysed by HPLC (LNT, LNnT, 2'-FL) or HPAEC (3'-SL, 6'-SL).

Example 1

Production of LNnT

Comparison of three LNnT producing strains: A) having chromosomally integrated β-1,3-N-acetylglucosaminyl transferase (IgtA) and a β-1,4-galactosyl transferase; B) having chromosomally integrated β-1,3-N-acetylglucosaminyl transferase (IgtA) and a plasmid incorporated β-1,4-galactosyl transferase with an antibiotic marker; and C) having chromosomally integrated 8-1,3-N-acetylglucosaminyl transferase (IgtA) and a plasmid comprising β-1,4-galactosyl transferase and nadC according to this invention. The strains contained the same β-1,4-galactosyl transferase and same copy number of chromosomally integrated IgtA. Cultivation of the strains was performed under identical conditions in shake flasks, for strains A and C in the absence of antibiotic whereas for strain B in the presence of antibiotic. The table below contains the by-product profiles of each culture relative to the values produced by strain A (taken as 100).

|  | strain A | strain B | strain C |
| --- | --- | --- | --- |
| pLNnH/LNnT | 100 | 106 | 45 |
| LNTri/LNnT | 100 | 78 | 19 |

The strain C according to the invention produced less pLNnH and LNTri relative to LNnT than strains A and B.

Example 2

Production of LNT

Comparison of two LNT producing strains: A) having plasmid incorporated β-1,3-N-acetylglucosaminyl transferase (IgtA) with and antibiotic marker (plasmid 1) and a plasmid incorporated β-1,3-galactosyl transferase with an antibiotic marker (plasmid 2); and B) having chromosomally integrated β-1,3-N-acetylglucosaminyl transferase (IgtA) and a plasmid comprising β-1,3-galactosyl transferase and nadC according to this invention. The strains contained the same β-1,3-galactosyl transferase. Cultivation of the strains was performed under identical conditions in shake flasks, for strain A in the presence of antibiotics whereas for strain B in the absence of antibiotic. The table below contains the product titre and by-product profile of each culture relative to the values produced by strain A (taken as 100).

|  | strain A | strain B |
| --- | --- | --- |
| LNT titre | 100 | 102 |
| LNTri/LNT | 100 | 18 |

The strain B according to the invention produced less LNTri by-product than strain A meanwhile the LNT productivity was maintained.

Example 3

Production of 2'-FL

Comparison of three 2'-FL producing strains: A) having chromosomally integrated α-1,2-fucosyl transferase (futC); B) having plasmid incorporated α-1,2-fucosyl transferase (futC) with an antibiotic marker; and C) having a plasmid comprising α-1,2-fucosyl transferase (futC) and nadC according to this invention. The strains contained same expression level of GDP-Fuc. Cultivation of the strains was performed under identical conditions in shake flasks, for strains A and C in the absence of antibiotic whereas for strain B in the presence of antibiotic. The table below contains the product titre of each culture relative to that produced by strain A (taken as 100).

|  | strain A | strain B | strain C |
| --- | --- | --- | --- |
| 2'-FL titre | 100 | 95 | 190 |

The strain C according to the invention was more productive than strains A and B.

Example 4

Production of 3'-SL

Comparison of three 3'-SL producing strains: A) having an α-2,3-sialyl transferase (nst) and neuBCA integrated in and expressed from the chromosome; B) having an α-2,3-sialyl transferase (nst) integrated in and expressed from the chromosome and neuBCA expressed from a plasmid containing an antibiotic marker; and C) having an α-2,3-sialyl transferase (nst) integrated in and expressed from the chromosome, and neuBCA and nadC expressed from the same plasmid according to this invention. The strains contained same copy number of chromosomally integrated nst. Cultivation of the strains was performed under identical conditions in shake flasks, for strains A and C in the absence of antibiotic whereas for strain B in the presence of antibiotic. The table below contains the product titre of each culture relative to that produced by strain A (taken as 100).

|  | strain A | strain B | strain C |
| --- | --- | --- | --- |
| 3'-SL titre | 100 | 261 | 330 |

The strain C according to the invention was more productive than strains A and B.

Example 5

Production of 6'-SL

Comparison of three 6'-SL producing strains: A) having an α-2,6-sialyl transferase (and neuBCA integrated in and expressed from the chromosome; B) having an α-2,6-sialyl transferase integrated in and expressed from the chromosome and neuBCA expressed from a plasmid containing an antibiotic marker; and C) having an α-2,6-sialyl transferase integrated in and expressed from the chromosome, and neuBCA and nadC expressed from the same plasmid according to this invention. The strains contained the same α-2,6-sialyl transferase in the same copy number. Cultivation of the strains was performed under identical conditions in shake flasks, for strains A and C in the absence of antibiotic whereas for strain B in the presence of antibiotic. The table below contains the product titre of each culture relative to that produced by strain A (taken as 100).

|  | strain A | strain B | strain C |
| --- | --- | --- | --- |
| 6'-SL titre | 100 | 122 | 140 |

The strain C according to the invention was more productive than strains A and B.

The invention claimed is:

1. A genetically modified cell for the production of an oligosaccharide, comprising
  a recombinant gene encoding a glycosyl transferase necessary for the synthesis of said oligosaccharide,
  a biosynthetic pathway to produce a monosaccharide nucleotide donor suitable to be transferred by said glycosyl transferase to an acceptor,
  chromosomal nadC gene is substantially inactivated or deleted, and
  an expression plasmid comprising
    said chromosomal nadC gene, or a DNA sequence encoding the product of said chromosomal nadC gene that is essential for the growth of said cell and DNA sequence(s) necessary for the expression of said DNA coding sequence; and
    a recombinant gene encoding a glycosyl transferase necessary for the synthesis of said oligosaccharide,
    or
    a recombinant gene expressing an enzyme necessary to produce a monosaccharide nucleotide donor in a biosynthetic pathway, which monosaccharide nucleotide donor is utilized in the synthesis of the oligosaccharide product.

2. The genetically modified cell of claim 1, which comprises only one plasmid.

3. The genetically modified cell of claim 1, wherein the chromosomal nadC gene is deleted.

4. The genetically modified cell of claim 1, wherein said oligosaccharide is a human milk oligosaccharide, and wherein the glycosyl transferase is selected from the group consisting of β-1,3-N-acetylglucosaminyl transferase, β-1,6-N-acetylglucosaminyl transferase, β-1,3-galactosyl transferase, β-1,4-galactosyl transferase, α-2,3-sialyl transferase, α-2,6-sialyl transferase, α-1,2-fucosyl transferase, α-1,3-fucosyl transferase and α-1,4 fucosyl transferase.

5. The genetically modified cell of claim 4, wherein the monosaccharide nucleotide donor is selected from the group consisting of UDP-Gal, UDP-GlcNAc, GDP-Fuc and CMP-sialic acid.

6. The genetically modified cell of claim 4, further comprising a functional lactose permease.

7. The genetically modified cell of claim 4, wherein said oligosaccharide is a non-acidic human milk oligosaccharide, and wherein said recombinant gene encoding a glycosyl transferase expresses a β-1,3-N-acetylglucosaminyl transferase, a β-1,6-N-acetylglucosaminyl transferase, a β-1,3-galactosyl transferase, a β-1,4-galactosyl transferase, an α-1,2-fucosyl transferase, an α-1,3-fucosyl transferase and/or an α-1,4 fucosyl transferase, and wherein said monosaccharide nucleotide donor is UDP-Gal, UDP-GlcNAc and/or GDP-Fuc.

8. The genetically modified cell of claim 7, wherein said non-acidic human milk oligosaccharide is non-fucosylated, and wherein said recombinant gene encoding a glycosyl transferase expresses a β-1,3-N-acetylglucosaminyl transferase, a β-1,3-galactosyl transferase and/or a β-1,4-galactosyl transferase, and wherein said monosaccharide nucleotide donor is UDP-Gal and/or UDP-GlcNAc.

9. The genetically modified cell of claim 8, wherein said non-acidic and non-fucosylated human milk oligosaccharide is LNT or LNnT, wherein said recombinant gene encoding a glycosyl transferase comprises a plasmid-borne recombinant gene encoding a first glycosyl transferase and another chromosomally integrated recombinant gene encoding a second glycosyl transferase.

10. The genetically modified cell of claim 7, wherein the non-acidic human milk oligosaccharide is 2'-FL or 3-FL, and wherein said recombinant gene encoding a glycosyl transferase expresses an α-1,2-fucosyl transferase or an α-1,3-fucosyl transferase, and said monosaccharide nucleotide donor is GDP-Fuc.

11. The genetically modified cell of claim 10, wherein said recombinant gene encoding a glycosyl transferase is plasmid-borne, and wherein the glycosyl transferase is an α-1,2-fucosyl transferase or an α-1,3-fucosyl transferase.

12. The genetically modified cell of claim 4, wherein said oligosaccharide is an acidic human milk oligosaccharide, wherein said recombinant gene encoding a glycosyl transferase is a sialyl transferase, and wherein said biosynthetic pathway produces CMP-sialic acid and comprises the genes encoding a UDP-GlcNAc 2-epimerase, a sialic acid synthase and a CMP-sialic acid synthetase.

13. The genetically modified cell of claim 12, wherein said acidic human milk oligosaccharide is 3'-SL or 6'-SL, and wherein said recombinant gene encoding a glycosyl transferase comprises a chromosomally integrated α-2,3-sialyl transferase or a chromosomally integrated α-2,6-sialyl transferase, and wherein said expression plasmid comprises genes encoding a plasmid-borne UDP-GlcNAc 2-epimerase, a plasmid-borne sialic acid synthase and a plasmid-borne CMP-sialic acid synthetase.

14. A method for making a recombinant oligosaccharide by glycosylating a carbohydrate acceptor, comprising the steps of:
   a) providing a cell of claim 1,
   b) culturing said cell in the presence of said acceptor, and
   c) separating said oligosaccharide from said cell, from the culture medium or from both.

15. The genetically modified cell of claim 8, wherein said non-acidic and non-fucosylated human milk oligosaccharide is selected from the group consisting of LNTri, LNT or LNnT.

16. The method of claim 14, wherein said carbohydrate acceptor is lactose.

17. The method of claim 14, wherein said recombinant oligosaccharide is a human milk oligosaccharide.

18. The method of claim 17, wherein said human milk oligosaccharide comprises 3 to 5 monosaccharide units.

19. The genetically modified cell of claim 6, wherein said functional lactose permease is LacY.

* * * * *